United States Patent [19]

Gericke et al.

[11] Patent Number: 5,753,680

[45] Date of Patent: May 19, 1998

[54] HETEROCYCLYL-BENZOYLGUANIDINES

[75] Inventors: Rolf Gericke, Seeheim-Jugenheim; Dieter Dorsch, Ober-Ramstadt; Manfred Baumgarth, Ober-Ramstadt; Klaus-Otto Minck, Ober-Ramstadt; Norbert Beier, Reinheim, all of Germany

[73] Assignee: Merck Patent Gesellschaft MIT Beschrankter Haftung, Darmstadt, Germany

[21] Appl. No.: 520,780

[22] Filed: Aug. 30, 1995

[30] Foreign Application Priority Data

Aug. 31, 1994 [DE] Germany ............... 44 30 861.2

[51] Int. Cl.$^6$ ............. A61K 31/445; C07D 211/44; C07D 233/64; C07D 213/68
[52] U.S. Cl. ............. 514/331; 514/255; 514/327; 514/357; 514/394; 514/399; 514/406; 514/427; 514/428; 514/429; 544/392; 546/221; 546/332; 548/309.7; 548/336.1; 548/377.1; 548/561; 548/569; 548/583; 549/491
[58] Field of Search ............. 514/327, 255, 514/357, 394, 399, 406, 331, 427, 428, 429; 544/392; 546/221, 332; 548/336.1, 561, 583, 309.7, 377.1, 569; 549/491

[56] References Cited

U.S. PATENT DOCUMENTS

| | | | |
|---|---|---|---|
| 5,091,394 | 2/1992 | Englert et al. | 514/331 |
| 5,292,755 | 3/1994 | Englert et al. | 514/331 |
| 5,364,868 | 11/1994 | Englert et al. | 514/331 |
| 5,373,024 | 12/1994 | Lang et al. | 514/618 |
| 5,461,066 | 10/1995 | Gericke et al. | 514/329 |

FOREIGN PATENT DOCUMENTS

| | | |
|---|---|---|
| 2089440 | 8/1993 | Canada . |
| 2130944 | 2/1995 | Canada . |

OTHER PUBLICATIONS

Schwark et al. "Preparation of Ureiodobenzoylguanidines as sodium–proton antiporter inhibitors" CA 123:55495d, 1995.
Weichert et al. "Preparation of ortho–substituted bonzoylguanidine sodium channel blocker"CA 123:55496c, 1995.
Kuno et al. "Guanidine derivatives as inhibitors of Na/H + exchange in cells"CA 123:256771a, 1995.

*Primary Examiner*—Ceila Chang
*Attorney, Agent, or Firm*—Millen, White, Zelane, & Branigan, P.C.

[57] ABSTRACT

Heterocyclyl-benzoylguanidines of the formula I

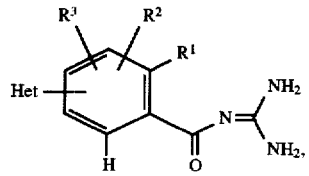

in which $R^1$, $R^2$, $R^3$ and Het have the meanings given herein, and physiologically unobjectionable salts thereof, display antiarrhythmic properties and act as inhibitors of the cellular $Na^+/H^+$ antiporter.

4 Claims, No Drawings

HETEROCYCLYL-BENZOYLGUANIDINES

The invention relates to ortho-substituted heterocyclyl-benzoylguanidines of the formula I

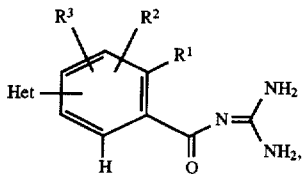

in which

R$^1$ is A, CF$_3$, CH$_2$F, CHF$_2$, C$_2$F$_5$, CN, NO$_2$, Hal, CCH or —X—R$^4$,

R$^2$ and R$^3$ are in each case independent of one another and are H, Hal, A, —X—R$^4$, CN, NO$_2$, CF$_3$, CH$_2$F, CHF$_2$, C$_2$F$_5$, CH$_2$CF$_3$, —SO$_n$—R$^6$, —SO$_2$NR$^4$R$^5$, Ph or OPh, R$^4$ is H, A, cycloalkyl of 5 to 7 carbon atoms, cycloalkylmethyl of 6 to 8 carbon atoms, CF$_3$, CH$_2$F, CHF$_2$, CH$_2$CF$_3$, Ph or —CH$_2$—Ph, R$^5$ is H or A, or else R$^4$ and R$^5$ together are alternatively alkylene of 4 to 5 carbon atoms, in which case one CH$_2$ group may also be replaced by O, S, NH, N—A or N—CH$_2$—Ph, R$^6$ is A or Ph, Het is a mono- or bicyclic saturated, unsaturated or aromatic heterocycle having 1 to 4 N, O and/or S atoms, attached via N or C, which may be unsubstituted or mono-, di- or trisubstituted by Hal, CF$_3$, A, —X—R$^4$, CN, NO$_2$ and/or carbonyl oxygen, A is alkyl of 1 to 6 carbon atoms, X is O, S or NR$^5$, Ph is unsubstituted phenyl or phenyl which is mono-, di- or trisubstituted by A, OA, NR$^4$R$^5$, Hal or CF$_3$, n is 1 or 2, and Hal is F, Cl, Br or I, and the physiologically unobjectionable salts thereof.

The object of the invention was to discover novel compounds having valuable properties, especially those compounds which can be used for preparing medicaments.

It has been found that the compounds of the formula I and their physiologically unobjectionable salts are well tolerated and possess valuable pharmacological properties.

The novel compounds are inhibitors of the cellular Na$^+$/H$^+$ antiporter, i.e. active compounds which inhibit the Na$^+$/H$^+$ exchange mechanism of cells (Düsing et al., Med. Klin. 87, 378–384 (1992)) and thus represent good antiarrhythmics which are particularly suitable for treatment of arrhythmias which occur as a result of lack of oxygen.

The best-known active compound of the acyl-guanidine group is amiloride. However, this substance primarily exhibits a hypotensive and saluretic effect, which is undesirable especially when treating disturbances of cardiac rhythm, while the antiarrhythmic properties are only very weakly pronounced.

In addition to this, structurally similar compounds are known, for example, from EP 04 16 499.

The invention relates to compounds of the formula I and to their physiologically unobjectionable salts.

The substances according to the invention of the present application exhibit a good cardioprotective effect and are therefore particularly suitable for the treatment of infarction, for infarction prophylaxis and for treating angina pectoris. Moreover, the substances counteract all pathological hypoxic and ischaemic damage, so that the diseases which are caused primarily or secondarily by such damage can be treated. The active compounds are likewise well suited to preventive applications.

Owing to the protective effects of these substances in pathological hypoxic or ischaemic situations, further possibilities result for using these compounds in association with surgical interventions, for protecting organs which are from time to time less well supplied, in association with organ transplants, for protecting the organs removed, in association with angioplastic vascular or cardiac surgery, for ischaemias of the nervous system, in association with the therapy of states of shock, and for profilactic-prevention of essential hypertension.

In addition, the compounds can also be employed as therapeutic agents in diseases arising from cell proliferation, such as arteriosclerosis, late complications in diabetes, tumoural diseases, fibrotic diseases, especially of the lung, liver and kidneys, and also organ hypertrophies and organ hyperplasias. Furthermore, the substances are suitable for diagnostic use, for the recognition of diseases which are accompanied by increased activity of the Na$^+$/H$^+$ antiporter, for example in erythrocytes, thrombocytes or leucocytes.

The effects of the compounds can be determined with the aid of methods which are known per se, as are indicated, for example, by N. Escobales and J. Figueroa in J. Membrane Biol. 120, 41–49 (1991) or by L. Counillon, W. Scholz, H. J. Lang and J. Pouyssegur in Mol. Pharmacol. 44, 1041–1045 (1993).

Examples of suitable experimental animals are mice, rats, guinea pigs, dogs, cats, monkeys or pigs.

The compounds may therefore be used as pharmaceutically active compounds in human and veterinary medicine. They may also be used as intermediates for the preparation of further pharmaceutical active compounds.

In the formulae given, A is a branched or unbranched alkyl group of 1–6, preferably 1–4, in particular 1, 2 or 3 carbon atoms, and specifically is preferably methyl, also preferably ethyl, propyl, isopropyl, butyl or isobutyl, with preference also being given to sec-butyl, tert-butyl, pentyl, isopentyl (3-methylbutyl), hexyl or isohexyl (4-methylpentyl).

R$^1$ is preferably A, OA or Hal, in particular Br or Cl, but also preferably CH$_2$F, CHF$_2$, CF$_3$ or C$_2$F$_5$.

R$^2$ and R$^3$ are preferably independent of one another, and are H, A—SO$_2$, A, CF$_3$, Cl, Br, CN or OA.

One of the two radicals is particularly preferably H$_3$C—SO$_2$—, whereas the other is preferably hydrogen. One of the two radicals R$^2$ and R$^3$ is preferably in position 3 or 5 of the benzoylguanidine group. If one of the radicals is A—SO$_2$—, then it is preferably in the meta position. Also particularly preferred is a benzoylguanidine group which has in position 3 a methylsulfonyl radical and in position 6 an alkyl group, preferably methyl or ethyl.

Like R$^5$, R$^4$ is preferably H or A.

If R$^4$ and R$^5$ together are alkylene, then the alkylene group is preferably unbranched, and specifically preferably —(CH$_2$)$_k$— in which k is 4 or 5,or else is preferably —(CH$_2$)$_2$—O—(CH$_2$)$_2$—, —(CH$_2$)$_2$—NH—(CH$_2$)$_2$—, —(CH$_2$)$_2$—NA—(CH$_2$)$_2$—, —CH$_2$—O—(CH$_2$)$_2$—, CH$_2$—NH—(CH$_2$)$_2$— or —CH$_2$—NA—(CH$_2$)$_2$— or —CO—(CH$_2$)$_3$—, —CO—(CH$_2$)$_4$— or —CH$_2$—CO—(CH$_2$)$_2$.

Ph is preferably unsubstituted phenyl or phenyl which is monosubstituted by Cl, Br, A, OA, NH$_2$, NHA, NA$_2$ or CF$_3$.

R$^6$ is preferably A, especially methyl, or else is preferably unsubstituted phenyl.

The radical X is preferably O or NH.

Het is preferably 2- or 3-furyl, 2- or 3-thienyl, 1-, 2- or 3-pyrrolyl, 1-, 2-, 4- or 5-imidazolyl, 1-, 3-, 4- or 5-pyrazolyl, 2-, 4- or 5-oxazolyl, 3-, 4- or 5-isoxazolyl, 2-, 4- or 5-thiazolyl, 3-, 4- or 5-isothiazolyl, 2-, 3- or 4-pyridyl, 2-, 4-, 5- or 6-pyrimidinyl, and also preferably, 1,2,3-triazol-1-, -4- or -5-yl, 1,2,4-triazol-1-, -3- or -5-yl, 1- or 5-tetrazolyl, 1,2,3-oxadiazol-4- or -5-yl, 1,2,4-oxadiazol-3- or -5-yl, 1,3,4-thiadiazol-2- or -5-yl, 1,2,4-thiadiazol-3- or -5-yl, 1,2,3-thiadiazol-4- or -5-yl, 2-, 3-, 4-, 5- or 6-2H-thiopyranyl, 2-, 3- or 4-4H-thiopyranyl, 3- or 4-pyridazinyl, pyrazinyl, 2-, 3-, 4-, 5-, 6- or 7-benzofuryl, 2-, 3-, 4-, 5-, 6- or 7-benzothienyl, 1-, 2-, 3-, 4-, 5-, 6- or 7-indolyl, 1-, 2-, 4- or 5-benzimidazolyl, 1-, 3-, 4-, 5-, 6- or 7-benzopyrazolyl, 2-, 4-, 5-, 6- or 7-benzoxazolyl, 3-, 4-, 5-, 6- or 7-benzisoxazolyl, 2-, 4-, 5-, 6- or 7-benzthiazolyl, 2-, 4-, 5-, 6- or 7-benzisothiazolyl, 4-, 5-, 6- or 7-benz-2,1,3-oxadiazolyl, 2-, 3-, 4-, 5-, 6-, 7- or 8-quinolyl, 1-, 3-, 4, 5-, 6-, 7- or 8-isoquinolyl, 1-, 2-, 3-, 4- or 9-carbazolyl, 1-, 2-, 3-, 4-, 5-, 6-, 7-, 8- or 9-acridinyl, 3-, 4-, 5-, 6-, 7- or 8-cinnolinyl, 2-, 4-, 5-, 6-, 7- or 8-quinazolinyl. The heterocyclic radicals may also be partially or completely hydrogenated. Het may therefore also be, for example, 2,3-dihydro-2-, -3-, -4- or -5-furyl, 2,5-dihydro-2-, -3-, -4- or -5-furyl, tetrahydro-2- or -3-furyl, 1,3-dioxolan-4-yl, tetrahydro-2- or -3-thienyl, 2,3-dihydro-1-, -2-, -3-, -4- or -5-pyrrolyl, 2,5-dihydro-1-, -2-, -3-, -4- or -5-pyrrolyl, 1-, 2- or 3-pyrrolidinyl, tetrahydro-1-, -2- or -4-imidazolyl, 2,3-dihydro-1-, -2-, -3-, -4- or -5-pyrazolyl, tetrahydro-1-, -3- or -4-pyrazolyl, 1,4-dihydro-1-, -2-, -3- or -4-pyridyl, 1,2,3,4-tetrahydro-1-, -2-, -3-, -4-, -5- or -6-pyridyl, 1,2,3,6-tetrahydro-1-, -2-, -3-, -4-, -5- or -6-pyridyl, 1-, 2-, 3- or 4-piperidyl, 2-, 3- or 4-morpholinyl, tetrahydro-2-, -3- or -4-pyranyl, 1,4-dioxanyl, 1,3-dioxan-2-, -4- or -5-yl, hexahydro-1-, -3- or -4-pyridazinyl, hexahydro-1-, -2-, -4- or -5-pyrimidinyl, 1-, 2- or 3-piperazinyl, 1,2,3,4-tetrahydro-1-, -2-, -3-, -4-, -5-, -6-, -7- or -8-quinolyl, 1,2,3,4-tetrahydro-1-, -2-, -3-, -4-, -5-, -6-, -7- or -8-isoquinolyl.

For the entire invention it holds that all radicals which occur more than once may be identical or different, i.e. are independent of one another.

Accordingly, the invention relates in particular to those compounds of the formula I in which at least one of the radicals mentioned has one of the preferred meanings indicated above. Some preferred groups of compounds may be expressed by the formulae Ia to Ih below, which correspond to the formula I and in which those radicals which are not designated in more detail have the meaning given in formula I, but in which in Ia $R^1$ is Hal, A or NH2 and $R^2$ is —$SO_2$—$CH_3$ or —$SO_2$—$NH_2$;

in Ib $R^1$ is A or Cl and $R^2$ is $SO_2$—$CH_3$;

in Ic $R^1$ is A and $R^2$ is $SO_2$—$CH_3$, in which case $R^2$ is para or ortho to $R^1$;

in Id Het is para to the amide group and is unsubstituted 1-imidazolyl or 1-imidazolyl which is mono- or disubstituted by A;

in Ie Het has the preferred definition under Id, and $R^2$ is $SO_2$—A and is meta to the amide group;

in If Het is 1-piperazinyl, 1-piperidyl, 1-pyrrolidinyl or 1-pyrrolyl which is unsubstituted or monosubstituted by A or OH, and $R^2$ is —$SO_2$—A and is meta to the amide group;

in Ig Het is pyridyl, oxodihydropyridyl or benzimidazolyl and is para to the guanidine carbonyl group, and $R^2$ is $SO_2$—A and $R^3$ is H;

in Ih $R^1$ is Hal and Het has one of the preferred meanings given under Id to Ig.

The invention also relates to a process for the preparation of compounds of the formula I according to claim 1, and of salts thereof, characterized in that a compound of the formula II

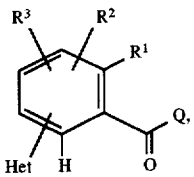

in which $R^1$, $R^2$ and Het have the meanings given above and

Q is Cl, Br, OA, O—CO—A, O—CO—Ph, OH or another reactive esterified OH group or leaving group which can easily be substituted nucleophilically, is reacted with guanidine, or in that a benzoylguanidine of the formula III

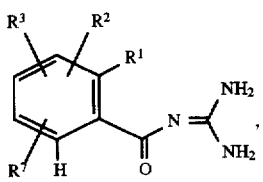

in which $R^1$, $R^2$ and $R^3$ have the meanings given above and $R^7$ is F, Cl, Br or I is reacted with a heterocyclic compound of the formula IV

 IV in which

Het has the meaning given and

D is H, $B(OH)_2$, trialkylsilyl, an alkali metal cation or ammonium, or else is a readily substitutable organometallic radical, or in that a compound which corresponds to the formula I except that it contains, instead of one or more hydrogen atoms, one or more reducible groups and/or one or more additional C—C and/or C—N bonds, is treated with a reducing agent, or in that a compound which corresponds to the formula I but which contains, instead of one or more hydrogen atoms, one or more solvolysable groups, is treated with a solvolysing agent, and/or in that a base of the formula I which is obtained is converted by treatment with acid into one of its salts.

The compounds of the formula I are otherwise prepared by methods known per se, as described in the literature (e.g. in the standard works such as Houben-Weyl, Methoden der organischen Chemie [Methods of organic chemistry], Georg-Thieme-Verlag, Stuttgart; Organic Reactions, John Wiley & Sons, Inc., New York; and in EP 0416499), and specifically under reaction conditions which are known and suitable for the abovementioned reactions. In this context, we can also be made of variants which are known per se and are not mentioned here in any more detail.

The starting compounds may if desired also be formed in situ such that they are not isolated from the reaction mixture but are instead immediately subjected to further reaction to give the compounds of the formula I.

Preferably, compounds of the formula I are prepared by reacting an activated carboxylic acid derivative of the formula II in which Q is particularly preferably Cl or —O—CH$_3$ with guanidine. Particularly suitable reaction variants are those in which the free carboxylic acid II (Q=OH) is converted in a manner known per se into the particular activated derivative and this is then reacted directly, without intermediate isolation, with guanidine. Methods in which intermediate isolation can be dispensed with are, for example, activation with carbonyldiimidazole, dicyclohexylcarbodiimide or the Mukayama variant (Angew. Chem. 91, 788–812 (1979)).

The carboxylic acids of the formula II are prepared, for example, by nucleophilic aromatic substitution starting from suitable benzoic acid derivatives or by reaction with appropriate heterocyclylboronic acids or the corresponding esters of the formula IV. The reaction is analogous to that of the compounds III and IV. It is described below.

Examples of particularly suitable compounds of the formula IV are 2-, 3- or 4-hydroxypyridine derivatives which may if desired possess further substituents, and also piperidine, piperazine, benzimidazole, imidazole, pyrazine, pyrimidine or pyridazine derivatives. Suitable reactants as compounds of the formula IV are, in particular, trimethylsilyl derivatives, alkali metal salts or boronic acid derivatives or esters thereof of the abovementioned heterocycles.

The reaction of a reactive carboxylic acid derivative of the formula II with guanidine is carried out in a manner known per se, preferably in a protic or aprotic polar or apolar inert organic solvent.

Suitable solvents are specified below for the reaction of the compounds III and IV. However, particularly preferred solvents are methanol, THF, dimethoxyethane, dioxane or mixtures which can be prepared therefrom, and also water. Suitable reaction temperatures are, for example, temperatures between 20° and the boiling point of the solvent. The reaction times are between 5 min and 12 h. It is advantageous to employ an acid scavenger in the reaction. Suitable such scavengers are all types of bases which do not interfere with the reaction itself. It is particularly suitable, however, to use inorganic bases such as potassium carbonate, or organic bases such as triethylamine or pyridine, or else an excess of the guanidine.

Compounds of the formula I above can also be prepared by reacting a benzoylguanidine of the formula III with a compound of the formula IV. The starting compounds of the formula III can be prepared in a simple manner by reaction of appropriately substituted benzoic acids, or reactive acid derivatives which can be derived therefrom such as, for example, acid halides, esters or anhydrides, with guanidine under reaction conditions which are known per se for amide preparation and are generally conventional. Particularly suitable reaction variants are again those indicated beforehand for the reaction of compound II with guanidine.

The compounds of the formula IV, like the methods for their preparation, are known per se. Where they are not known, they can be prepared by the methods which are known per se.

The preparation of the compound II and the reaction of the compound III with a compound of the formula IV are carried out in a manner known per se, preferably in a protic or aprotic polar inert organic solvent.

A preferred variant, however, comprises reacting the reactants with one another directly, without addition of a solvent.

In the preparation of II or in the reaction of III with IV it is likewise advantageous to operate in the presence of a base or with an excess of the basic component. Examples of suitable bases are preferably alkali metal hydroxides or alkaline earth metal hydroxides, carbonates, alcoholates or organic bases such as triethylamine or pyridine, which may also be employed in excess and in this case act simultaneously as solvent.

Particularly suitable inert solvents are alcohols such as methanol, ethanol, isopropanol, n-butanol or tert-butanol; ethers such as diethyl ether, diisopropyl ether, tetrahydrofuran (THF) or dioxane; glycol ethers such as ethylene glycol monomethyl or monoethyl ether (methylglycol or ethylglycol), ethylene glycol dimethyl ether (diglyme); ketones such as acetone or butanone; nitriles such as acetonitrile; nitro compounds such as nitromethane or nitrobenzene; esters such as ethyl acetate; amides such as hexamethylphosphoric triamide; sulfoxides such as dimethyl sulfoxide (DMSO); chlorinated hydrocarbons such as dichloromethane, chloroform, trichloroethylene, 1,2-dichloroethane or carbon tetrachloride; and hydrocarbons such as benzene, toluene or xylene. Also suitable are mixtures of these solvents with one another.

Furthermore, the compounds of the formula I can be obtained by liberating them from their functional derivatives by solvolysis, especially hydrolysis, or by hydrogenolysis.

Preferred starting compounds for the solvolysis or hydrogenolysis are those which conform to the formula I but which contain, instead of one or more free amino and/or hydroxyl groups, corresponding protected amino and/or hydroxyl groups, preferably those which carry an amino-protective group instead of a hydrogen atom connected to a nitrogen atom, and especially those which carry, instead of an HN group, an R'—N group in which R' is an amino-protective group, and/or those which carry, instead of the hydrogen atom of a hydroxyl group, a hydroxyl-protective group, for example those which correspond to the formula I but carry, instead of an OH group, a group OR" in which R" is a hydroxyl-protective group.

It is also possible for two or more—identical or different—protected amino and/or hydroxyl groups to be present in the molecule of the starting compound. If the protective groups present are different from one another, then in many cases they can be eliminated selectively.

The term "amino-protective group" is generally known and relates to groups which are suitable for protecting (for blocking) an amino group against chemical reactions, but which are readily removable after the desired chemical reaction has been carried out at a different site of the molecule. Typical of such groups are, in particular, unsubstituted or substituted acyl, aryl (e.g. 2,4-dinitrophenyl (DNP); aralkoxymethyl (e.g. benzyloxymethyl (BOM)) or aralkyl groups (e.g. benzyl, 4-nitrobenzyl, triphenylmethyl.

Since the amino-protective groups are removed after the desired reaction (or sequence of reactions), their nature and size is otherwise not critical; however, preference is given to those of 1–20 carbon atoms, in particular 1–8 carbon atoms. In conjunction with the present process, the term "acyl group" should be understood in the broadest sense. It encompasses acyl groups derived from aliphatic, araliphatic, aromatic or heterocyclic carboxylic acids or sulfonic acids and also, in particular, alkoxycarbonyl, aryloxycarbonyl and, especially, aralkoxycarbonyl groups. Examples of such acyl groups are alkanoyl, such as acetyl, propionyl and butyryl; aralkanoyl such as phenylacetyl; aroyl such as benzoyl or tolyl; aryloxyalkanoyl such as phenoxyacetyl; alkoxycarbonyl such as methoxycarbonyl, ethoxycarbonyl, 2,2,2-trichloroethoxycarbonyl, isopropoxycarbonyl, tert-butoxycarbonyl (BOC) or 2-iodoethoxycarbonyl; aralkyloxycarbonyl such as benzyloxycarbonyl (CBZ), 4-methoxybenzyloxycarbonyl or 9-fluorenylmethoxycarbonyl (FMOC). Preferred amino-protective groups are BOC, DNP and BOM, and also CBZ, benzyl and acetyl.

The term "hydroxyl-protective group" is likewise generally known and relates to groups which are suitable for protecting a hydroxyl group against chemical reactions but which are readily removable after the desired chemical reaction has been carried out at a different site in the molecule. Typical of such groups are the abovementioned unsubstituted or substituted aryl, aralkyl or acyl groups, and also alkyl groups. The nature and size of the hydroxyl-protective groups is not critical, since they are removed again after the desired chemical reaction or sequence of reactions; preference is given to groups having 1 to 20 carbon atoms, in particular 1–10 carbon atoms. Examples of hydroxyl-protective groups include tert-butyl, benzyl, p-nitrobenzoyl, p-toluenesulfonyl and acetyl, with benzyl and acetyl being particularly preferred.

The functional derivatives of the compounds of the formula I to be used as starting compounds can be prepared by conventional methods as described, for example, in the abovementioned standard works and patent applications, for example by reaction of compounds of the formulae II and III in which, however, at least one of these compounds contains a protective group instead of a hydrogen atom.

The liberation of the compounds of the formula I from their functional derivatives is carried out, depending on the protective group used, for example using strong acids, advantageously with trifluoroacetic acid or perchloric acid, or else with other strong inorganic acids such as hydrochloric acid or sulfuric acid, strong organic carboxylic acids such as trichloroacetic acid, or sulfonic acids such as benzene- or p-toluenesulfonic acid. The presence of an additional inert solvent is possible but not always necessary.

Suitable inert solvents are preferably organic, for example carboxylic, acids such as acetic acid, ethers such as tetrahydrofuran (THF) or dioxane, amides such as dimethylformamide (DMF), halogenated hydrocarbons such as dichloromethane, and also alcohols such as methanol, ethanol or isopropanol, and water. Also suitable are mixtures of the abovementioned solvents. Trifluoroacetic acid is preferably used in excess without the addition of a further solvent, while perchloric acid is used in the form of a mixture of acetic acid and 70% perchloric acid in a ratio of 9:1. The reaction temperatures for the cleavage are advantageously between about 0 and about 500; it is preferably carried out at between 15 and 300 (room temperature).

The BOC group can be cleaved off, for example, using 40% trifluoroacetic acid in dichloromethane or with from about 3 to 5 N HCl in dioxane at 15–60°, the FMOC group using an about 5–20% solution of dimethylamine, diethylamine or piperidine in DMF at 15–50°. The DNP group can also be cleaved off, for example, using an about 3–10% solution of 2-mercaptoethanol in DMF/water at 15–30°.

Protective groups which can be removed by hydrogenolysis (e.g. BOM, CBZ or benzyl) can be cleaved off, for example, by treatment with hydrogen in the presence of a catalyst (for example a noble metal catalyst such as palladium, advantageously on a support such as charcoal). Suitable solvents in this context are those mentioned above, particular examples being alcohols such as methanol or ethanol or amides such as DMF. The hydrogenolysis is generally carried out at temperatures between about 0 and 1000 and at pressures of between about 1 and 200 bar, preferably at 20–30° and 1–10 bar. Hydrogenolysis of the CBZ group, for example, is highly successful over 5–10% Pd/C in methanol at 20–30°.

Furthermore, a base of the formula I can be converted with an acid into the corresponding acid addition salt. Suitable acids for this reaction are those which give physiological unobjectionable salts. Thus it is possible to use inorganic acids, for example sulfuric acid, nitric acid, hydrohalic acids such as hydrochloric acid or hydrobromic acid, phosphoric acids such as orthophosphoric acid, sulfamic acid, and also organic acids, especially aliphatic, alicyclic, araliphatic, aromatic or heterocyclic mono- or polybasic carboxylic, sulfonic or sulfuric acids, examples being formic acid, acetic acid, propionic acid, pivalic acid, diethylacetic acid, malonic acid, succinic acid, pimelic acid, fumaric acid, maleic acid, lactic acid, tartaric acid, malic acid, benzoic acid, salicylic acid, 2- or 3-phenylpropionic acid, citric acid, gluconic acid, ascorbic acid, nicotinic acid, isonicotinic acid, methane- or ethanesulfonic acid, ethanedisulfonic acid, 2-hydroxyethanesulfonic acid, benzenesulfonic acid, p-toluenesulfonic acid, naphthalene mono- and -disulfonic acids, and lauryl-sulfuric acid.

The compounds of the formula I and their physiologically unobjectionable salts may be used to produce pharmaceutical preparations, especially by non-chemical means such as mechanical mixing. In this context hey can be brought, together with at least one solid, liquid and/or semi-liquid carrier substance or auxiliary and, if desired, in combination with one or more additional active compounds, into a suitable dosage form.

The invention relates, furthermore, to compositions, especially pharmaceutical preparations, which contain at least one compound of the formula I and/or one of its physiologically unobjectionable salts.

These preparations may be used as medicaments in human or veterinary medicine. Suitable carrier substances are organic or inorganic substances which are suitable for enteral (e.g. oral), parenteral or topical administration and which do not react with the novel compounds, for example water, vegetable oils, benzyl alcohols, polyethylene glycols, glycerol triacetate, gelatine, carbohydrates such as lactose or starch, magnesium stearate, talc, lanolin and petroleum jelly. For oral application use is made, in particular, of tablets, coated tablets, capsules, syrups, juices or drops, for rectal application use is made of suppositories, and for parenteral application use is made of solutions, preferably oily or aqueous solutions, and also suspensions, emulsions or implants, for topical application of ointments, creams, pastes, lotions, gels, sprays, foams, aerosols, solutions (e.g. solutions in alcohols such as ethanol or isopropanol, acetonitrile, DMF, dimethylacetamide, 1,2-propanediol or mixtures thereof with one another and/or with water) or powders. The novel compounds may also be lyophilized and the resulting lyophilizates used, for example, to produce preparations for injections.

For topical application in particular, liposomal preparations are also suitable. The preparations indicated may be sterilized and/or contain auxiliaries such as glidants, preservatives, stabilizers and/or wetting agents, emulsifiers, salts for influencing the osmotic pressure, buffer substances, colorants, flavourings and/or aroma substances. If desired they may also contain one or more other active compounds, for example one or more vitamins.

The compounds of the formula I and their physiologically unobjectionable salts can be administered to humans or animals, especially to mammals such as monkeys, dogs, cats, rats or mice and can be used in the therapeutic treatment of the human or animal body and for controlling diseases, especially for the therapy and/or prophylaxis of disturbances of the cardiovascular system. They are therefore suitable for the treatment of arrhythmias, especially those induced by lack of oxygen, of angina pectoris, infarctions, ischaemias of the nervous systems such as, for example, stroke or cerebral oedemas, of states of shock and also for preventive treatment.

The substances can also be employed as therapeutic agents in diseases in which cell proliferation plays a role, such as arteriosclerosis, late complications in diabetes, tumour diseases, fibroses and organ hypertrophies and -hyperplasias.

In this context the substances according to the invention are generally administered in analogy to known antiarrhythmics, such as aprindine, preferably in doses of between about 0.01 and 5 mg, in particular between 0.02 and 0.5 mg, per dosage unit. The daily dose is preferably between about 0.0001 and 0.1, in particular between 0.0003 and 0.01, mg/kg of body weight. The specific dose for each particular patient depends, however, on a wide variety of factors, for example on the effectiveness of the specific compound employed, on the age, body weight, general condition of health, sex, on the diet, on the time and route of administration, on the speed of excretion, on the combination of medicaments and on the severity of the particular disease to which the therapy is applied. Oral application is preferred.

The "physiologically unobjectionable salts" herein include the "physiologically acceptable salts" and "pharmaceutically acceptable salts".

Without further elaboration, it is believed that one skilled in the art can, using the preceding description, utilize the present invention to its fullest extent. The following preferred specific embodiments are, therefore, to be construed as merely illustrative, and not limitative of the remainder of the disclosure in any way whatsoever.

In the foregoing and in the following examples, all temperatures are set forth uncorrected in degrees Celsius and unless otherwise indicated, all parts and percentages are by weight.

The entire disclosure of all applications, patents and publications, cited above and below, and of corresponding application German application number P 44 30 861.2, are hereby incorporated by reference.

In the Examples which follow, "customary workup" denotes:

If required, water is added and extraction takes place with an organic solvent such as ethyl acetate, the phases are separated, the organic phase is dried over sodium sulfate, filtered and concentrated by evaporation, and the residue is purified by chromatography and/or crystallization.

EXAMPLE 1

A solution of 2.54 g of guanidine and 2.41 g of methyl 2-methyl-4-(1-imidazolyl)-5-methylsulfonylbenzoate [obtainable by reacting 2-methyl-4-chloro-5-methylsulfonylbenzoic acid with imidazole in the presence of NaH in N-methylpyrrolidone followed by esterification] in 20 ml of methanol is stirred at 500 for 3 hours. Water is then added to the reaction mixture, and the crude product which precipitates out is filtered off with suction and recrystallized from methanol. N-Diaminomethylene-2-methyl-4-(1-imidazolyl)-5-methyl-sulfonylbenzamide, m.p. 236°, is obtained.

The following are obtained analogously by reacting guanidine with methyl 2-chloro-4-(1-imidazolyl)-5-methylsulfonylbenzoate:

N-diaminomethylene-2-chloro-4-(1-imidazolyl)-5-methylsulfonylbenzamide, m.p. 220°;

with methyl 2-ethyl-4-(1-piperidyl)-5-methylsulfonylbenzoate:

N-diaminomethylene-2-ethyl-4-(1-piperidyl)-5-methylsulfonylbenzamide, m.p. 218–220°.

with methyl 2-methyl-4-(1-piperidyl)-5-methylsulfonylbenzoate:

N-diaminomethylene-2-methyl-4-(1-piperidyl)-5-methylsulfonylbenzamide, m.p. 224°;

with methyl 2-chlor-4-(4-amino-piperidino)-5-methylsulfonylbenzoate:

N-diaminomethylene-2-methyl-4-(4-amino-piperidino)-5-methylsulfonylbenzamider, m.p. 305–310° (dihydrochloride);

with methyl 2-chloro-4-(4-amino-piperidino)-5-methylsulfonylbenzoate:

N-diaminomethylene-2-chloro-4-(4-amino-piperidino)-5-methylsulfonylbenzamide, m.p. 302–305° (dihydrochloride);

with methyl 2-chloro-4-(5-pyrimidinyl)-5-methylsulfonylbenzoate:

N-diaminomethylene-2-chloro-4-(5-pyrimidinyl)-5-methylsulfonylbenzamide;

with methyl 2-chloro-4-(2-pyridazinyl)-5-methylsulfonylbenzoate:

N-diaminomethylene-2-chloro-4-(2-pyridazinyl)-5-methylsulfonylbenzamide;

with methyl 2-chloro-4-(3-pyridazinyl)-5-methylsulfonylbenzoate:

N-diaminomethylene-2-chloro-4-(3-pyridazinyl)-5-methylsulfonylbenzamide;

with methyl 2-chloro-4-(4-pyridazinyl)-5-methylsulfonylbenzoate:

N-diaminomethylene-2-chloro-4-(4-pyridazinyl)-5-methylsulfonylbenzamide;

with methyl 2-methyl-4-(1,6-dihydro-6-oxo-3-pyridazinyl)-5-methylsulfonylbenzoate:

N-diaminomethylene-2-methyl-4-(1,6-dihydro-6-oxo-3-pyridazinyl)-5-methylsulfonylbenzamide;

with methyl 2-chloro-4-(1,6-dihydro-6-oxo-3-pyridazinyl)-5-methylsulfonylbenzoate:

N-diaminomethylene-2-chloro-4-(1,6-dihydro-6-oxo-3-pyridazinyl)-5-methylsulfonylbenzamide;

with methyl 3-ethyl-4-(1,6-dihydro-6-oxo-3-pyridazinyl)-5-methylsulfonylbenzoate:

N-diaminomethylene-2-ethyl-4-(1,6-dihydro-6-oxo-3-pyridazinyl)-5-methylsulfonylbenzamide;

with methyl 2-amino-4-(1,6-dihydro-6-oxo-3-pyridazinyl)-5-methylsulfonylbenzoate:

N-diaminomethylene-2-amino-4-(1,6-dihydro-6-oxo-3-pyridazinyl)-5-methylsulfonylbenzamide;

with methyl 2-fluoro-4-(1,4-dihydro-4-oxo-1-pyridyl)-5-methylsulfonylbenzoate:

N-diaminomethylene-2-fluoro-4-(1,4-dihydro-4-oxo-1-pyridyl)-5-methylsulfonylbenzamide;

with methyl 2-chloro-4-(2-pyridyl)-5-methylsulfonylbenzoate:

N-diaminomethylene-2-chloro-4-(2-pyridyl)-5-methylsulfonylbenzamide;

with methyl 2-chloro-4-(3-pyridyl)-5-methylsulfonylbenzoate:

N-diaminomethylene-2-chloro-4-(2-pyridyl)-5-methylsulfonylbenzamide;

with methyl 2-chloro-4- (4-pyridyl) -5-methylsulfonylbenzoate:

N-diaminomethylene-2-chloro-4-(4-pyridyl)-5-methylsulfonylbenzamide;

with methyl 2-methyl-4-(1,4-dihydro-4-oxo-1-pyridyl)-5-methylsulfonylbenzoate:

N-diaminomethylene-2-methyl-4-(1,4-dihydro-4-oxo-1-pyridyl)-5-methylsulfonylbenzamide;
with methyl 2-chloro-4- (1,4-dihydro-4-oxo-1-pyridyl)-5-methylsulfonylbenzoate:

N-diaminomethylene-2-chloro-4-(1,4-dihydro-4-oxo-1-pyridyl)-5-methylsulfonylbenzamide;
with methyl 2-ethyl-4- (1,4-dihydro-4-oxo-1-pyridyl)-5-methylsulfonylbenzoate:

N-diaminomethylene-2-ethyl-4-(1,4-dihydro-4-oxo-1-pyridyl)-5-methylsulfonylbenzamide;
with methyl 2-amino-4- (1,4-dihydro-4-oxo-1-pyridyl)-5-methylsulfonylbenzoate:

N-diaminomethylene-2-amino-4-(1,4-dihydro-4-oxo-1-pyridyl)-5-methylsulfonylbenzamide;
with methyl 2-propyl-4-(1,4-dihydro-4-oxo-1-pyridyl)-5-methylsulfonylbenzoate:

N-diaminomethylene-2-propyl-4-(1,4-dihydro-4-oxo-1-pyridyl)-5-methylsulfonylbenzamide.

EXAMPLE 2

4 g of N-diaminomethylene-2-methyl-4-(1-imidazolyl)-5-methylsulfonylbenzamide [obtainable according to Example 1] are treated with 1-molar aqueous HCl solution for 1 hour and then freeze-dried. N-Diaminomethylene-2-methyl-4-(1-imidazolyl)-5-methyl-sulfonylbenzamide dihydrochloride is obtained.

The following are obtained analogously by treatment with aqueous HCl and subsequent freeze-drying:
from N-diaminomethylene-2-chloro-4-(1-imidazolyl)-5-methylsulfonylbenzamide: the dihydrochloride;
from N-diaminomethylene-2-methyl-4-(1-piperidyl)-5-methylsulfonylbenzamide: the hydrochloride, m.p. 247°;
from N-diaminomethylene-2-methyl-4-(4-methyl-1-imidazolyl)-5-methylsulfonylbenzamide: the dihydrochloride, m.p. 236°.

EXAMPLE 3

A solution of 4.2 g of methyl 2-methyl-4-(3-hydroxy-1-piperidyl)-5-methylsulfonylbenzoate [obtainable by reacting 3-hydroxypiperidine with 2-methyl-4-chloro-5-methylsulfonylbenzoic acid followed by esterification] and 3.89 g of guanidine in 20 ml of methanol is stirred at 50° over a period of three hours. The solution is cooled, water is added, the mixture is stirred for 1 hour and the precipitate which is formed is separated off. After recrystallization from acetone/methanol, N-diaminomethylene-2-methyl-4-(3-hydroxy-1-piperidyl)-5-methylsulfonylbenzamide is obtained, m.p. 194–196°.

The following are obtained analogously by reacting guanidine
with methyl 2-chloro-4-(3-hydroxy-1-piperidyl)-5-methylsulfonylbenzoate:

N-diaminomethylene-2-chloro-4-(3-hydroxy-1-piperidyl)-5-methylsulfonylbenzamide, m.p. 170°;
with methyl 2-amino-4-(3-hydroxy-1-piperidyl)-5-methylsulfonylbenzoate:

N-diaminomethylene-2-amino-4-(3-hydroxy-1-piperidyl)-5-methylsulfonylbenzamide, m.p. 232–233°;
with methyl 2-ethyl-4-(3-hydroxy-1-piperidyl)-5-methylsulfonylbenzoate:

N-diaminomethylene-2-ethyl-4-(3-hydroxy-1-piperidyl)-5-methylsulfonylbenzamide, m.p. 222–225°.

EXAMPLE 4

3 g of N-diaminomethylene-2-ethyl-4-chloro-5-methylsulfonylbenzamide [obtainable by reacting methyl 2-methyl-4-chloro-5-methylsulfonylbenzoate with guanidine] are heated with 30 ml of 4-trimethylsilyloxypyridine in the presence of 3 g of $K_2CO_3$ in a closed tube at 135° for five hours. The mixture is cooled, the excess silylpyridine is removed by decanting, and the residue is triturated with ether and filtered off with suction. The solid residue is then dissolved in methanol and chromatographed over silica gel (ethyl acetate/methanol). Recrystallization from isopropanol and ethanol gives N-diaminomethylene-2-ethyl-4-(1,4-dihydro-4-oxo-1-pyridyl)-5-methylsulfonylbenzamide, m.p. 261–263°.

EXAMPLE 5

2.1 g of N-diaminomethylene-2-ethyl-4-(1,4-dihydro-4-oxo-1-pyridyl)-5-methylsulfonylbenzamide [obtainable according to Example 4] are treated with 1-molar aqueous HCl solution for 1 hour and then freeze-dried. N-Diaminomethylene-2-ethyl-4-(1,4-dihydro-4-oxo-1-pyridyl)-5-methylsulfonylbenzamide hydrochloride is obtained, m.p. >270°.

EXAMPLE 6

In analogy to Example 1, by reacting guanidine with methyl 2,3-di-methyl-4-(1-imidazolyl)-5-methyl-sulfonylbenzoate [obtainable by reacting 2,3-di-methyl-4-chloro-5-methylsulfonylbenzoic acid with 1-trimethylsilyl-imidazole followed by esterification], N-diaminomethylene-2,3-di-methyl-4-(1-imidazolyl)-5-methylsulfonylbenzamide is obtained, m.p. 249°.

The following are obtained analogously by reacting guanidine
with methyl 2-methyl-4-(4-methyl-1-imidazolyl)-5-methylsulfonylbenzoate:

N-diaminomethylene-2-methyl-4-(4-methyl-1-imidazolyl)-5-methylsulfonylbenzamide;
with methyl 2,3,4-trimethyl-5-(1-pyrrolyl)-benzoate:

N-diaminomethylene-2,3,4-trimethyl-5-(1-pyrrolyl)-benzamide, m.p. 218°; m.p. (methanesulphonate) 205–206°;
with methyl 2-methyl-4-(2-methyl-1-imidazolyl)-5-methylsulfonylbenzoate:

N-diaminomethylene-2-methyl-4-(2-methyl-1-imidazolyl)-5-methylsulfonylbenzamide, m.p. 251°;
with methyl 2-ethyl-4-(1-imidazolyl)-5-methylsulfonylbenzoate:

N-diaminomethylene-2-ethyl-4-(1-imidazolyl)-5-methylsulfonylbenzamide;
with methyl 2-methyl-4-(1-pyrrolyl)-5-methylsulfonylbenzoate:

N-diaminomethylene-2-methyl-4-(1-pyrrolyl)-5-methylsulfonylbenzamide, m.p. 210–211°;
with methyl 2-methyl-4-(1-benzimidazolyl)-5-methylsulfonylbenzoate:

N-diaminomethylene-2-methyl-4-(1-benzimidazolyl)-5-methylsulfonylbenzamide;
with methyl 2-ethyl-4-(4-methyl-1-imidazolyl)-5-methylsulfonylbenzoate:

N-diaminomethylene-2-ethyl-4-(4-methyl-1-imidazolyl)-5-methylsulfonylbenzamide;
with methyl 2-ethyl-4-(2,4-dimethyl-1-imidazolyl)-5-methylsulfonylbenzoate:

N-diamino-2-ethyl-4-(2,4-dimethyl-1-imidazolyl)-5-methylsulfonylbenzamide;
with methyl 2-amino-4-(1-piperidinyl)-5-methylsulfonylbenzoate:

N-diaminomethylene-2-amino-4-(1-piperidyl)-5-methylsulfonylbenzamide, m.p. 240–241°; hydrochloride m.p. 305–310°;

with methyl 2-methyl-4-(1-pyrrolidinyl)-5-methylsulfonylbenzoate:

N-diaminomethylene-2-methyl-4-(1-pyrrolidinyl)-5-methylsulfonylbenzamide, m.p. 222–224°;

with methyl 2-methyl-5-(1-benzimidazolyl)-benzoate:

N-diaminomethylene-2-methyl-5-(1-benzimidazolyl)-benzamide;

with methyl 2-methyl-4-(2-furanyl)-5-methyl-sulfonylbenzoate:

N-diaminomethylene-2-methyl-4-(2-furanyl)-5-methylsulfonylbenzamide, m.p. 185–186°, methansulfonate m.p. 280–281°;

with methyl 2-amino-4-(2,4-dimethyl-1-imidazolyl)-5-methylsulfonylbenzoate:

N-diaminomethylene-2-amino-4-(2,4-dimethyl-1-imidazolyl)-5-methylsulfonylbenzamide;

with methyl 2-methyl-4-(1-pyrazolyl)-5-methylsulfonylbenzoate:

N-diaminomethylene-2-methyl-4-(1-pyrazolyl)-5-methylsulfonylbenzamide, m.p. 225–226°;

with methyl 2-methyl-4-(1-pyrrolyl)-5-methylsulfonylbenzoate:

N-diaminomethylene-2-methyl-3-(1-pyrrolyl)-5-methylsulfonylbenzamide, m.p. 216°;

with methyl 2-amino-4-(1-benzimidazolyl)-5-methylsulfonylbenzoate:

N-diaminomethylene-2-amino-4-(1-benzimidazolyl)-5-methylsulfonylbenzamide;

with methyl 2-methyl-4-(-1-imidazolyl)-5-nitrobenzoate:

N-diaminomethylene-2-methyl-4-(1-imidazolyl)-5-nitrobenzamide, m.p. 244°;

with methyl 2-methyl-3-(1-pyrrolyl)-4-chloro-5-methylsulfonyl-benzoat:

N-Diaminomethylen-2-methyl-3-(1-pyrrolyl)-4-chloro-5-methylsulfonylbenzamide, m.p. 250°;

with methyl 2-nitro-4-(2,4-dimethyl-1-imidazolyl)-5-methylsulfonylbenzoate:

N-diaminomethylene-2-nitro-4-(2,4-dimethyl-1-imidazolyl)-5-methylsulfonylbenzamide;

with methyl 2-nitro-4-(1-imidazolyl)-5-methylsulfonylbenzoate:

N-diaminomethylene-2-nitro-4-(1-imidazolyl)-5-methylsulfonylbenzamide;

with methyl 2-nitro-4-(1-pyrrolyl)-5-methylsulfonylbenzoate:

N-diaminomethylene-2-nitro-4-(1-pyrrolyl)-5-methylsulfonylbenzamide;

with methyl 2-nitro-4-(1-benzimidazolyl)-5-methylsulfonylbenzoate:

N-diaminomethylene-2-nitro-4-(1-benzimidazolyl)-5-methylsulfonylbenzamide;

with methyl 2-fluoromethyl-4-(4-methyl-1-imidazolyl)-5-methylsulfonylbenzoate:

N-diaminomethylene-2-fluoromethyl-4-(4-methyl-1-imidazolyl)-5-methylsulfonylbenzamide;

with methyl 2-fluoromethyl-4-(2,4-dimethyl-1-imidazolyl)-5-methylsulfonylbenzoate:

N-diaminomethylene-2-fluoromethyl-4-(2,4-dimethyl-1-imidazolyl)-5-methylsulfonylbenzamide;

with methyl 2-fluoromethyl-4-(1-imidazolyl)-5-methyl-sulfonylbenzoate:

N-diaminomethylene-2-fluoromethyl-4-(1-imidazolyl)-5-methylsulfonylbenzamide;

with methyl 2-fluoromethyl-4-(1-pyrrolyl)-5-methyl-sulfonylbenzoate:

N-diaminomethylene-2-fluoromethyl-4-(1-pyrrolyl)-5-methylsulfonylbenzamide;

with methyl 2-fluoromethyl-4-(1-benzimidazolyl)-5-methylsulfonylbenzoate:

N-diaminomethylene-2-fluoromethyl-4-(1-benzimidazolyl)-5-methylsulfonylbenzamide;

with methyl 2-difluoromethyl-4-(4-methyl-1-imidazolyl)-5-methylsulfonylbenzoate:

N-diaminomethylene-2-difluoromethyl-4-(4-methyl-1-imidazolyl)-5-methylsulfonylbenzamide;

with methyl 2-difluoromethyl-4-(2,4-dimethyl-1-imidazolyl)-5-methylsulfonylbenzoate:

N-diaminomethylene-2-difluoromethyl-4-(2,4-dimethyl-1-imidazolyl) -5-methylsulfonylbenzamide;

with methyl 2-difluoromethyl-4-(1-imidazolyl)-5-methylsulfonylbenzoate:

N-diaminomethylene-2-difluoromethyl-4-(1-imidazolyl)-5-methylsulfonylbenzamide;

with methyl 2-difluoromethyl-4-(1-pyrrolyl)-5-methylsulfonylbenzoate:

N-diaminomethylene-2-difluoromethyl-4-(1-pyrrolyl)-5-methylsulfonylbenzamide;

with methyl 2-difluoromethyl-4-(1-benzimidazolyl)-5-methylsulfonylbenzoate:

N-diaminomethylene-2-difluoromethyl-4-(1-benzimidazolyl)-5-methylsulfonylbenzamide;

with methyl 2-trifluoromethyl-4-(4-methyl-1-imidazolyl)-5-methylsulfonylbenzoate:

N-diaminomethylene-2-trifluoromethyl-4-(4-methyl-1-imidazolyl)-5-methylsulfonylbenzamide;

with methyl 2-trifluoromethyl-4-(2,4-dimethyl-1-imidazolyl)-5-methylsulfonylbenzoate:

N-diaminomethylene-2-trifluoromethyl-4-(2,4-dimethyl-1-imidazolyl)-5-methylsulfonylbenzamide;

with methyl 2-trifluoromethyl-4-(1-imidazolyl)-5-methylsulfonylbenzoate:

N-diaminomethylene-2-trifluoromethyl-4-(1-imidazolyl) -5-methylsulfonylbenzamide;

with methyl 2-trifluoro-4-(1-pyrrolyl)-5-methylsulfonylbenzoate:

N-diaminomethylene-2-trifluoromethyl-4-(1-pyrrolyl)-5-methylsulfonylbenzamide;

with methyl 2-trifluoromethyl-4-(1-benzimidazolyl)-5-methylsulfonylbenzoate:

N-diaminomethylene-2-trifluoromethyl-4-(1-benzimidazolyl)-5-methylsulfonylbenzamide;

with methyl 2-cyano-4-(4-methyl-1-imidazolyl) -5-methylsulfonylbenzoate:

N-diaminomethylene-2-cyano-4-(4-methyl-1-imidazolyl) -5-methylsulfonylbenzamide;

with methyl 2-cyano-4-(2,4-dimethyl-1-imidazolyl)-5-methylsulfonylbenzoate:

N-diaminomethylene-2-cyano-4-(2,4-dimethyl-1-imidazolyl)-5-methylsulfonylbenzamide;

with methyl 2-cyano-4-(1-imidazolyl)-5-methylsulfonylbenzoate:

N-diaminomethylene-2-cyano-4-(1-imidazolyl)-5-methylsulfonylbenzamide;

with methyl 2-cyano-4-(1-pyrrolyl)-5-methylsulfonylbenzoate:

N-diaminomethylene-2-cyano-4-(1-pyrrolyl)-5-methylsulfonylbenzamide;

with methyl 2-cyano-4-(1-benzimidazolyl)-5-methylsulfonylbenzoate:

N-diaminomethylene-2-cyano-4-(1-benzimidazolyl)-5-methylsulfonylbenzamide;

with methyl 2-methoxy-4-(4-methyl-1-imidazolyl)-5-methylsulfonylbenzoate:

N-diaminomethylene-2-methoxy-4-(4-methyl-1-imidazolyl)-5-methylsulfonylbenzamide;

with methyl 2-methoxy-4-(2,4-dimethyl-1-imidazolyl)-5-methylsulfonylbenzoate:
N-diaminomethylene-2-methoxy-4-(2,4-dimethyl-1-imidazolyl)-5-methylsulfonylbenzamide;
with methyl 2-methoxy-4-(1-imidazolyl)-5-methylsulfonylbenzoate:
N-diaminomethylene-2-methoxy-4-(1-imidazolyl)-5-methylsulfonylbenzamide;
with methyl 2-methoxy-4-(1-pyrrolyl)-5-methylsulfonylbenzoate:
N-diaminomethylene-2-methoxy-4-(1-pyrrolyl)-5-methylsulfonylbenzamide;
with methyl 2-methoxy-4-(1-benzimidazolyl)-5-methylsulfonylbenzoate:
N-diaminomethylene-2-methoxy-4-(1-benzimidazolyl)-5-methylsulfonylbenzamide;
with methyl 2-ethynyl-4-(4-methyl-i-imidazolyl)-5-methylsulfonylbenzoate:
N-diaminomethylene-2-ethynyl-4-(4-methyl-1-imidazolyl)-5-methylsulfonylbenzamide;
with methyl 2-ethynyl-4-(2,4-dimethyl-1-imidazolyl)-5-methylsulfonylbenzoate:
N-diaminomethylene-2-ethynyl-4-(2,4-dimethyl-1-imidazolyl)-5-methylsulfonylbenzamide;
with methyl 2-ethynyl-4-(1-imidazolyl)-5-methylsulfonylbenzoate:
N-diaminomethylene-2-ethynyl-4-(1-imidazolyl)-5-methylsulfonylbenzamide;
with methyl 2-ethynyl-4-(1-pyrrolyl)-5-methylsulfonylbenzoate:
N-diaminomethylene-2-ethynyl-4-(1-pyrrolyl)-5-methylsulfonylbenzamide;
with methyl 2-ethynyl-4-(1-benzimidazolyl)-5-methylsulfonylbenzoate:
N-diaminomethylene-2-ethynyl-4-(1-benzimidazolyl)-5-methylsulfonylbenzamide.

EXAMPLE 7

1.0 g of methyl 2-amino-4-(3-pyridyl)-5-methylsulfonylbenzoate [obtainable by reacting methyl 2-amino-4-bromo-5-methylsulfonylbenzoate with pyridine-3-boronic acid] is dissolved in 15 ml of 1-methylpyrrolidone and the solution is stirred for 15 min. Subsequently 0.9 g of guanidinium chloride and 2.6 ml of diisopropylethylamine are added and the mixture is stirred at room temperature for one hour. Customary workup gives N-diaminomethylene-2-amino-4-(3-pyridyl)-5-methylsulfonylbenzamide.

The following are obtained analogously by reaction with guanidinium chloride:
from methyl 2-amino-4-(3-pyridyl)-5-methylsulfonylbenzoate:
N-diaminomethylene-2-amino-4-(3-pyridyl)-5-methylsulfonylbenzamide;
from methyl 2-cyano-4-(3-pyridyl)-5-methylsulfonylbenzoate:
N-diaminomethylene-2-cyano-4-(3-pyridyl)-5-methylsulfonylbenzamide; from methyl 2-methoxy-4-(3-pyridyl)-5-methylsulfonylbenzoate:
N-diaminomethylene-2-methoxy-4-(3-pyridyl)-5-methylsulfonylbenzamide;
from methyl 2-ethynyl-4-(3-pyridyl)-5-methylsulfonylbenzoate:
N-diaminomethylene-2-ethynyl-4-(3-pyridyl)-5-methylsulfonylbenzamide;

from methyl 2-fluoromethyl-4-(3-pyridyl)-5-methylsulfonylbenzoate:
N-diaminomethylene-2-fluoromethyl-4-(3-pyridyl)-5-methylsulfonylbenzamide;
from methyl 2-difluoromethyl-4-(3-pyridyl)-5-methylsulfonylbenzoate:
N-diaminomethylene-2-difluoromethyl-4-(3-pyridyl)-5-methylsulfonylbenzamide;
from methyl 2-trifluoromethyl-4-(3-pyridyl)-5-methylsulfonylbenzoate:
N-diaminomethylene-2-trifluoromethyl-4-(3-pyridyl)-5-methylsulfonylbenzamide;
from methyl 2-amino-4-(1,4-dihydro-4-oxo-1-pyridyl)-5-methylsulfonylbenzoate:
N-diaminomethylene-2-amino-4-(1,4-dihydro-4-oxo-1-pyridyl)-5-methylsulfonylbenzamide;
from methyl 2-methoxy-4-(4-aminopiperidino)-5-methylsulfonylbenzoate:
N-diaminomethylene-2-methoxy-4-(4-aminopiperidino)-5-methylsulfonylbenzamide, m.p. 270° (hydrochloride);
from methyl 2-cyano-4-(1,4-dihydro-4-oxo-1-pyridyl)-5-methylsulfonylbenzoate:
N-diaminomethylene-2-cyano-4-(1,4-dihydro-4-oxo-1-pyridyl)-5-methylsulfonylbenzamide;
from methyl 2-methoxy-4-(1,4-dihydro-4-oxo-1-pyridyl)-5-methylsulfonylbenzoate:
N-diaminomethylene-2-methoxy-4-(1,4-dihydro-4-oxo-1-pyridyl)-5-methylsulfonylbenzamide;
from methyl 2-ethynyl-4-(1,4-dihydro-4-oxo-1-pyridyl)-5-methylsulfonylbenzoate:
N-diaminomethylene-2-ethynyl-4-(1,4-dihydro-4-oxo-1-pyridyl)-5-methylsulfonylbenzamide;
from methyl 2-fluoromethyl-4-(1,4-dihydro-4-oxo-1-pyridyl)-5-methylsulfonylbenzoate:
N-diaminomethylene-2-fluoromethyl-4-(1,4-dihydro-4-oxo-1-pyridyl)-5-methylsulfonylbenzamide;
from methyl 2-difluoromethyl-4-(1,4-dihydro-4-oxo-1-pyridyl)-5-methylsulfonylbenzoate:
N-diaminomethylene-2-difluoromethyl-4-(1,4-dihydro-4-oxo-1-pyridyl)-5-methylsulfonylbenzamide;
from methyl 2-trifluoromethyl-4-(1,4-dihydro-4-oxo-1-pyridyl)-5-methylsulfonylbenzoate:
N-diaminomethylene-2-trifluoromethyl-4-(1,4-dihydro-4-oxo-1-pyridyl)-5-methylsulfonylbenzamide;
from methyl 2-methyl-4-piperidino-5-nitro-benzoate:
N-diaminomethylene-2-methyl-4-piperidino-5-nitro-benzamide, m.p. 174°;
from methyl 2-amino-4-(1-benzimidazolyl)-5-methylsulfonylbenzoate:
N-diaminomethylene-2-amino-4-(1-benzimidazolyl)-5-methylsulfonylbenzamide;
from methyl 2-cyano-4-(1-benzimidazolyl)-5-methylsulfonylbenzoate:
N-diaminomethylene-2-cyano-4-(1-benzimidazolyl)-5-methylsulfonylbenzamide;
from methyl 2-methoxy-4-(1-benzimidazolyl)-5-methylsulfonylbenzoate:
N-diaminomethylene-2-methoxy-4-(1-benzimidazolyl)-5-methylsulfonylbenzamide;
from methyl 2-ethynyl-4-(1-benzimidazolyl)-5-methylsulfonylbenzoate:
N-diaminomethylene-2-ethynyl-4-(1-benzimidazolyl)-5-methylsulfonylbenzamide;
from methyl 2-fluoromethyl-4-(1-benzimidazolyl)-5-methylsulfonylbenzoate:

N-diaminomethylene-2-fluoromethyl-4-(1-benzimidazolyl)-5-methylsulfonylbenzamide;
from methyl 2-difluoromethyl-4-(1-benzimidazolyl)-5-methylsulfonylbenzoate:
N-diaminomethylene-2-difluoromethyl-4-(1-benzimidazolyl)-5-methylsulfonylbenzamide;
from methyl 2-trifluoromethyl-4-(1-benzimidazolyl)-5-methylsulfonylbenzoate:
N-diaminomethylene-2-trifluoromethyl-4-(1-benzimidazolyl)-5-methylsulfonylbenzamide.

EXAMPLE 8

In analogy to Example 1, by reaction of guanidine with methyl 2-fluoro-4-(2-methyl-1-imidazolyl)-5-methylsulfonylbenzoate [obtainable by reacting 2-fluoro-4-chloro-5-methylsulfonylbenzoic acid with 2-methylimidazole followed by esterification], N-diaminomethylene-2-fluoro-4-(2-methyl-1-imidazolyl)-5-methylsulfonylbenzamide is obtained.

The following are obtained analogously by reacting guanidine
with methyl 2-fluoro-4-(4-methyl-1-imidazolyl)-5-methylsulfonylbenzoate:
N-diaminomethylene-2-fluoro-4-(4-methyl-1-imidazolyl)-5-methylsulfonylbenzamide;
with methyl 2-fluoro-4-(2,4-dimethyl-1-imidazolyl)-5-methylsulfonylbenzoate:
N-diaminomethylene-2-fluoro-4-(2,4-dimethyl-1-imidazolyl)-5-methylsulfonylbenzamide;
with methyl 2-fluoro-4-(1-imidazolyl)-5-methylsulfonylbenzoate:
N-diaminomethylene-2-fluoro-4-(1-imidazolyl)-5-methylsulfonyl benzamide;
with methyl 2-fluoro-4-(1-pyrrolyl)-5-methylsulfonylbenzoate:
N-diaminomethylene-2-fluoro-4-(1-imidazolyl)-5-methylsulfonylbenzamide;
with methyl 2-fluoro-4-(1-benzimidazolyl)-5-methylsulfonylbenzoate:
N-diaminomethylene-2-fluoro-4-(1-benzimidazolyl)-5-methylsulfonylbenzamide;
with methyl 2-fluoro-4-(1-piperidyl)-5-methylsulfonylbenzoate:
N-diaminomethylene-2-fluoro-4-(1-piperidyl)-5-methylsulfonylbenzamide;
with methyl 2-fluoro-4-(3-pyridyl)-5-methylsulfonylbenzoate:
N-diaminomethylene-2-fluoro-4-(3-pyridyl)-5-methylsulfonylbenzamide;
with methyl 2-fluoro-4-(2-pyridyl)-5-methylsulfonylbenzoate:
N-diaminomethylene-2-fluoro-4-(2-pyridyl)-5-methylsulfonylbenzamide;
with methyl 2-fluoro-4-(1,4-dihydro-4-oxo-1-pyridyl)-5-methylsulfonylbenzoate:
N-diaminomethylene-2-fluoro-4-(1,4-dihydro-4-oxo-1-pyridyl)-5-methylsulfonylbenzamide;
with methyl 2-methyl-3-methylsulfonyl-4-(4-methyl-1-imidazolyl)-benzoate:
N-diaminomethylene-2-methyl-4-(4-methyl-1-imidazolyl)-3-methylsulfonylbenzamide;
with methyl 2-methyl-3-methylsulfonyl-4-(2-methyl-1-imidazolyl)-benzoate:
N-diaminomethylene-2-methyl-4-(2-methyl-1-imidazolyl)-3-methylsulfonylbenzamide;
with methyl 2-methyl-3-methylsulfonyl-4-(2,4-dimethyl-1-imidazolyl)-benzoate:
N-diaminomethylene-2-methyl-3-methylsulfonyl-4-(2,4-dimethyl-i-imidazolyl) -benzamide;
with methyl 2-methyl-3-methylsulfonyl-4-(1-imidazolyl)-benzoate:
N-diaminomethylene-2-methyl-3-methylsulfonyl-4-(1-imidazolyl)-benzamide;
with methyl 2-methyl-3-methylsulfonyl-4-(1-pyrrolyl)-benzoate:
N-diaminomethylene-2-methyl-3-methylsulfonyl-4-(1-pyrrolyl)-benzamide;
with methyl 2-methyl-3-methylsulfonyl-4-(1-benzimidazolyl)-benzoate:
N-diaminomethylene-2-methyl-3-methylsulfonyl-4-(1-benzimidazolyl)-benzamide;
with methyl 2-methyl-3-methylsulfonyl-4-(1-piperidyl)-benzoate:
N-diaminomethylene-2-methyl-3-methylsulfonyl-4-(1-piperidyl)-benzamide;
with methyl 2-methyl-3-methylsulfonyl-4-(3-hydroxy-1-piperidyl)-benzoate:
N-diaminomethylene-2-methyl-3-methylsulfonyl-4-(3-hydroxy-1-piperidyl)-benzamide;
with methyl 2-methyl-3-methylsulfonyl-4-(3-pyridyl)-benzoate:
N-diaminomethylene-2-methyl-3-methylsulfonyl-4-(3-pyridyl)-benzamide;
with methyl 2-methyl-3-methylsulfonyl-4-(2-pyridyl)-benzoate:
N-diaminomethylene-2-methyl-3-methylsulfonyl-4-(2-pyridyl)-benzamide;
with methyl 2-methyl-3-methylsulfonyl-4-(1,4-dihydro-4-oxo-1-pyridyl)-benzoate:
N-diaminomethylene-2-methyl-3-methylsulfonyl-4-(1,4-dihydro-4-oxo-1-pyridyl)-benzamide; with methyl 2-ethyl-3-methylsulfonyl-4-(4-methyl-1-imidazolyl)-benzoate:
N-diaminomethylene-2-ethyl-3-methylsulfonyl-4-(4-methyl-1-imidazolyl)-benzamide;
with methyl 2-ethyl-3-methylsulfonyl-4-(2-methyl-1-imidazolyl)-benzoate:
N-diaminomethylene-2-ethyl-4-(2-methyl-1-imidazolyl)-3-methylsulfonylbenzamide;
with methyl 2-ethyl-3-methylsulfonyl-4-(2,4-dimethyl-1-imidazolyl)-benzoate:
N-diaminomethylene-2-ethyl-3-methylsulfonyl-4-(2,4-dimethyl-i-imidazolyl)-benzamide;
with methyl 2-ethyl-3-methylsulfonyl-4-(1-imidazolyl)-benzoate:
N-diaminomethylene-2-ethyl-3-methylsulfonyl-4-(1-imidazolyl)-benzamide;
with methyl 2-ethyl-3-methylsulfonyl-4-(1-pyrrolyl)-benzoate:
N-diaminomethylene-2-ethyl-3-methylsulfonyl-4-(1-pyrrolyl)-benzamide;
with methyl 2-ethyl-3-methylsulfonyl-4-(1-benzimidazolyl)-benzoate:
N-diaminomethylene-2-ethyl-3-methylsulfonyl-4-(1-benzimidazolyl)-benzamide;
with methyl 2-ethyl-3-methylsulfonyl-4-(1-piperidyl)-benzoate:
N-diaminomethylene-2-ethyl-3-methylsulfonyl-4-(1-piperidyl)-benzamide;

with methyl 2-ethyl-3-methylsulfonyl-4-(3-hydroxy-1-piperidyl)-benzoate:
   N-diaminomethylene-2-ethyl-3-methylsulfonyl-4-(3-hydroxy-1-piperidyl)-benzamide;
with methyl 2-ethyl-3-methylsulfonyl-4-(3-pyridyl)-benzoate:
   N-diaminomethylene-2-ethyl-3-methylsulfonyl-4-(3-pyridyl)-benzamide;
with methyl 2-ethyl-3-methylsulfonyl-4-(2-pyridyl)-benzoate:
   N-diaminomethylene-2-ethyl-3-methylsulfonyl-4-(2-pyridyl)-benzamide;
with methyl 2-ethyl-3-methylsulfonyl-4-(1,4-dihydro-4-oxo-1-pyridyl)-benzoate:
   N-diaminomethylene-2-ethyl-3-methylsulfonyl-4-(1,4-dihydro-4-oxo-1-pyridyl)-benzamide.

The Examples which follow relate to pharmaceutical preparations.

Example A: Injection vials

A solution of 100 g of an active compound of the formula I and 5 g of disodium hydrogen phosphate in 3 l of double-distilled water is adjusted to a pH of 6.5 using 2 N hydrochloric acid, subjected to sterile filtration, dispensed into injection vials and lyophilized and the vials are sealed in a sterile manner. Each injection vial contains 5 mg of active compound.

Example B: Suppositories

A mixture of 20 mg of an active compound of the formula I is melted with 100 g of soya lecithin and 1400 g of cocoa butter and the mixture is poured into moulds and allowed to cool. Each suppository contains 20 mg of active compound.

Example C: Solution

A solution is prepared from 1 g of an active compound of the formula I, 9.38 g of $NaH_2PO_4 \times 2H_2O$, 28.48 g of $Na_2HPO_4 \times 12H_2O$ and 0.1 g of benzalkonium chloride in 940 ml of double-distilled water. The solution is adjusted to a pH of 6.8, made up to 1 l and sterilized by irradiation. This solution can be used in the form of eye drops.

Example D: Ointment 500 mg of an active compound of the formula I are mixed with 99.5 g of petroleum jelly under aseptic conditions.

Example E: Tablets

A mixture of 1 kg of active compound of the formula I, 4 kg of lactose, 1.2 kg of potato starch, 0.2 kg of talc and 0.1 kg of magnesium stearate is pressed in a customary manner to give tablets, such that each tablet contains 10 mg of active compound.

Example F: Coated tablets

Tablets are pressed in analogy to Example E and are then coated in a conventional manner with a coating of sucrose, potato starch, talc, tragacanth and colorant.

Example G: Capsules

Hard gelatin capsules are filled in a customary manner with 2 kg of active compound of the formula I such that each capsule contains 20 mg of the active compound.

Example H: Ampoules

A solution of 1 kg of active compound of the formula I in 60 l of double-distilled water is dispensed into ampoules and lyophilized under aseptic conditions, and the ampoules are sealed in a sterile manner. Each ampoule contains 10 mg of active compound.

The preceding examples can be repeated with similar success by substituting the generically or specifically described reactants and/or operating conditions of this invention for those used in the preceding examples.

From the foregoing description, one skilled in the art can easily ascertain the essential characteristics of this invention, and without departing from the spirit and scope thereof, can make various changes and modifications of the invention to adapt it to various usages and conditions.

We claim:

1. Heterocyclylbenzoylguanidine of the formula I

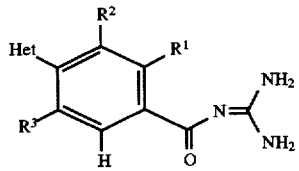

in which $R^1$ is A, $CF_3$, CHF, $CHF_2$, $C_2F_5$, CN, $NO_2$, Hal, —C≡CH or —X—$R^4$, $R^2$ is in each case independent of one another and are H, Hal, A, —X—$R^4$, CN, $NO_2$, $CF_3$, $CH_2F$, $CHF_2$, $C_2F_5$, $CH_2CF_3$, —$SO_n$—$R^6$, —$SO_2NR^4R^5$, Ph or OPh, $R^4$ is H, A, cycloallyl of 5 to 7 carbon atoms, cycloalkylmethyl of 6 to 8 carbon atoms, $CF_3$, $CH_2F$, $CHF_2$, $CH_2CF_3$, Ph or —$CH_2$—Ph, $R^5$ is H or A, or else $R^4$ and $R^5$ together are alkylene of 4 to 5 carbon atoms, in which case one $CH_2$ group may also be replaced by O, S, NH, N—A or N—$CH_2$—Ph, $R^6$ is A or Ph, Het is imidazolyl, piperazinyl, piperidyl, pyrrolyl, pyridyl, oxodihydropyridyl, benzimidazolyl, pyrazolyl, furanyl and pyrrolidinyl, A is alkyl of 1 to 6 carbon atoms, X is O or S, Ph is unsubstituted phenyl or phenyl which is mono-, di- or trisubstituted by A, OA, $NR^4R^5$, F, Cl, Br, I or $CF_3$, n is 1 or 2, and Hal is F, Cl, Br or I.

2. A compound selected from the group consisting of
   (a) N-Diaminomethylene-2-ethyl-4-(1-imidazolyl)-5-methylsulfonylbenzamide;
   (b) N-diaminomethylene-2-methyl-4-(1-imidazolyl)-5-methylsulfonylbenzamide;
   (c) N-diaminomethylene-2-methyl-4-(3-hydroxypiperidino)-5-methylsulfonylbenzamide;
   (d) N-diaminomethylene-2-ethyl-4-(3-pyridyl)-5-methylsulfonylbenzamide;
   (e) N-diaminomethylene-2-ethyl-4-(2-pyridyl)-5-methylsulfonylbenzamide;
   (f) N-diaminomethylene-2-ethyl-4-(1,4-dihydro-4-oxo-1-pyridyl)-5-methylsulfonylbenzamide;

and the physiologically acceptable salts thereof.

3. Process for the preparation of heterocyclylbenzoylguanidine derivatives of the formula I according to claim 1 and of their salts, characterized in that a compound of the formula II

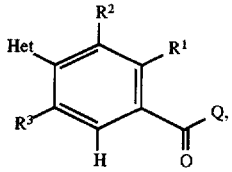

II in which $R^1$, $R^2$, $R^3$ and Het have the meanings given above and

Q is Cl, Br, OA, O—CO—A, O—CO—Ph, OH or another reactive esterified OH group or leaving group which can easily be substituted nucleophilically, is reacted with guanidine, or in that a benzoylguanidine of the formula III

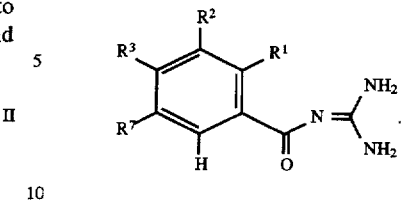

4. Pharmaceutical preparation, which comprises at least one compound of the general formula I according to claim 1 or one of it physiologically acceptable salts.

* * * * *